(12) United States Patent
Della Negra et al.

(10) Patent No.: US 7,838,704 B2
(45) Date of Patent: Nov. 23, 2010

(54) PROCESS FOR THE SYNTHESIS OF TERBINAFINE AND DERIVATIVES THEREOF

(75) Inventors: Federico Della Negra, Alte Di Montecchio Maggiore (IT); Cristiano Grandini, Alte Di Montecchio Maggiore (IT); Mariano Stivanello, Alte Di Montecchio Maggiore (IT)

(73) Assignee: F.I.S. Fabbrica Italiana Sintetici S.p.A., Milan (IT)

( * ) Notice: Subject to any disclaimer, the term of this patent is extended or adjusted under 35 U.S.C. 154(b) by 696 days.

(21) Appl. No.: 11/628,252

(22) PCT Filed: Mar. 4, 2005

(86) PCT No.: PCT/IT2005/000121

§ 371 (c)(1),
(2), (4) Date: May 7, 2007

(87) PCT Pub. No.: WO2005/121155

PCT Pub. Date: Dec. 22, 2005

(65) Prior Publication Data

US 2007/0244336 A1    Oct. 18, 2007

(30) Foreign Application Priority Data

Jun. 9, 2004   (IT) .......................... MI2004A1154

(51) Int. Cl.
*C07F 7/10* (2006.01)
*C07C 209/68* (2006.01)

(52) U.S. Cl. ........................ 564/458; 564/305; 556/410

(58) Field of Classification Search ...................... None
See application file for complete search history.

(56) References Cited

U.S. PATENT DOCUMENTS 5,817,875 A    10/1998   Karimian et al.
7,288,678 B2 * 10/2007   Tarquini et al. ............. 564/387

FOREIGN PATENT DOCUMENTS

EP            1 236 709        9/2002

OTHER PUBLICATIONS

Oh et al., 41 Tetra. Lett., 8513-16 (2000).*
Alami et al., 37 Tetra. Lett., 57-58 (1996).*
Schmerling, 71 J.A.C.S., 701-03 (1949).*
Li et al., 51 J. Org. Chem., 4354-56 (1986).*
Quillinan et al., J.C.S. Chem. Comm., 1030-31 (1974).*
Vippagunta et al., Advanced Drug Delivery Reviews 2001.*
Morissette et al., Advanced Drug Delivery Reviews, 2004.*
Negishi Acc. Chem. Res. 1982, 15, 340-348.*
King et al., "Highly General Stereo-,Regio-, and Chemo-Selective Synthesis of Terminal and Internal Conjugated Enzyme by the PD-Catalysed Reaction of Alkynylzinc Reagents with Alkenyl Halides" Journal of the Chemical Society, Chemical Communications, Chemical Society, Letchworth, GB, pp. 683-684, 1977.
Vicart et al., "Application of (2E,4E)-5-Bromo-2, 4-Pentadienal in Palladium Catalyzed Cross-Coupling: Easy Access to (2E,4E)-2, 4-Dienals" Synlett, Thieme Verlag, Stuttgart, DE, vol. 4, pp. 411-412, Apr. 1998.
Alami et al., "Weakly Ligated Palladium Complexes PdCl2(RCN)2 in Piperdine: Versatile Catalysts for Sonogashira Reaction of Vinyl Chlorides at Room Temperature" Journal of Organometallic Chemistry, Elsevier-Sequoia S.A. Lausanne, CH, vol. 624, No. 1-2, pp. 114-123, Apr. 1, 2001.
Oh et al., "Efficient Coupling Reactions of Lithium Alkynyl(Triisopropoxy) Borates with Aryl Halides: Application to the Antifungal Terbinafine Synthesis" Tetrahedron Letters, Elsevier Science Publishers, Amsterdam, NL, vol. 41, No. 44, pp. 8513-8516, Oct. 28, 2000.
Rudisill et al., "Synthesis of Terbinafine. A Palladium Catalysed Vinyl Iodide-Ethynylstannane Coupling" Tetrahedron Letters, Elsevier Science Publishers, Amsterdam, NL, vol. 29, No. 13, pp. 1509-1512, 1988.
Beutler et al., "Die Entwicklung Eines Neuen, Umweltgerechten Produktionsprozesses Fuer Terbinafin" Chimia, Aarau, CH, vol. 50, No. 4, pp. 154-156, 1996.
Stutz et al., "Synthesis and Antifungal Activity of (E)-N-)(6,6-Dimethyl-2-Hepten-4-Ynyl)-N-Met,Hyl-1-Naphthalenemethanamine (SF 86-327) and Related Allylamine Derivatives with Enhanced Oral Activity" Journal of Medicinal Chemistry, American Chemical Society, Washington, US, vol. 27, No. 12, pp. 1539-1543, 1984.
Jong et al., "A New Route to the Synthesis of Terbinafine" Bulletin of the Korean Chemical Society, Korean Chemical Society, Seoul, KR, vol. 18, No. 11, pp. 1218-1220, 1997.

* cited by examiner

*Primary Examiner*—Daniel M Sullivan
*Assistant Examiner*—Yevegeny Valenrod
(74) *Attorney, Agent, or Firm*—Dickstein Shapiro LLP

(57) ABSTRACT

The present invention relates to a synthetic method for terbinafine and analogues thereof using metal catalysts, preferably Ni(II) salts and/or complexes.

24 Claims, No Drawings

PROCESS FOR THE SYNTHESIS OF TERBINAFINE AND DERIVATIVES THEREOF

FIELD OF THE INVENTION

The present invention describes a synthesis method for the production of terbinafine and derivatives thereof.

BACKGROUND ART

Terbinafine, chemically defined as (E)-N-(6,6-dimethyl-2-hepten-4-inyl)-N-methyl-1-naphthalene-methylamine and having the structure (1), is an antimicotic drug for topical and oral use, having the following chemical structure:

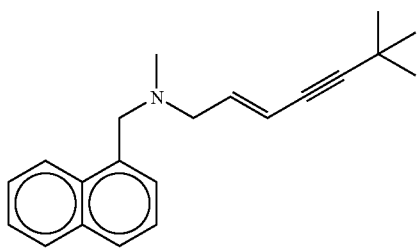

(1)

The first, laboratory scale, synthetic route for this compound is described in European patent EP 0 024 587 and consists in reacting the lithium salt of tert-butylacetylene with acrolein, followed by an allylic bromination/rearrangement reaction, to give the intermediate (E+Z)-1-bromo-6,6-dimethyl-hepten-4-ine, which is then condensed with (1-naphthylmethyl)methanamine to give a mixture of (E+Z)-N-(6,6-dimethyl-2-hepten-4-inyl)-N-methyl-1-naphthalene-methylamine from which terbinafine (1) is then isolated, in the hydrochloride form. This synthetic route has several drawbacks if used on the industrial scale; firstly, the use of acrolein, a toxic substance, difficult to obtain and transport in moderate industrial amounts and, above all, in the final stage, the formation of a mixture of E+Z isomers which must be separated by crystallisation, thus leading to a drastic reduction in the process yield.

More recently, various alternative synthetic routes have been identified, leading to more industrially convenient processes. For example, the article by Alami et al., Tetrahedron Lett., 37, 57-58, (1996) describes the following synthetic method:

Scheme 1

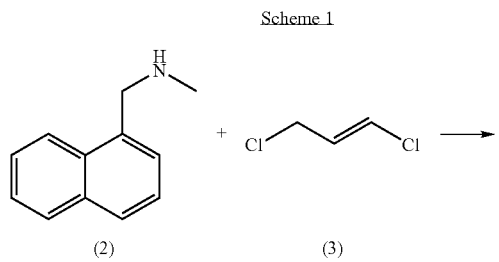

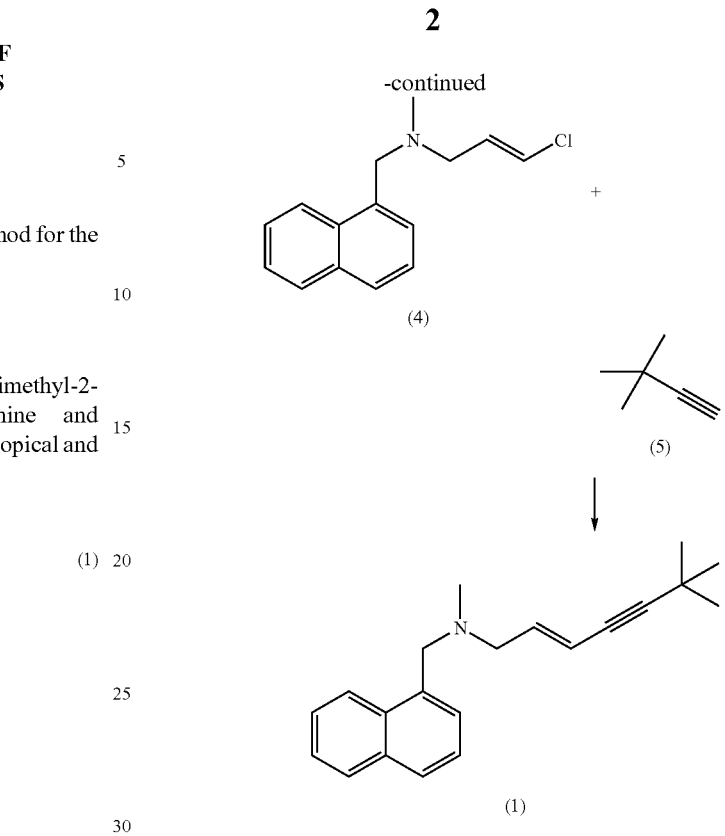

This process comprises the initial alkylation of (1-naphthylmethyl)methanamine (2), with 1,3-dichloropropene (3), raw materials which are both commercially available, to give the intermediate N-(3-chloro-2-propenyl)-N-methyl-1-naphthalene-methylamine (4).

This latter intermediate undergoes a "Heck-coupling" type reaction with tert-butylacetylene (5) in the presence of palladium or copper catalysts, to give terbinafine (1). Essentially analogous processes are described in patents EP 0 421 302 and EP 0 645 369 and in the recent patent applications WO 01/77064, WO 02/02503 and EP 1 236 709. The latter report novel processes for final coupling using other types of catalysts, or particular reaction conditions. This synthetic route is brief, simply executed and generally characterised by good overall yield. On the other hand, it has low industrial applicability since it uses tert-butylacetylene (5), a reagent that is still rather costly, together with palladium complexes and/or salts (for example tetrakis(triphenylphosphine)palladium(0) or dichloro-bis(triphenylphosphine)palladium(II)), themselves also rather expensive. This has an influence over the final cost of the drug, with obvious social consequences.

SUMMARY OF THE INVENTION

The present invention provides a synthetic method which allows overcoming all the above mentioned problems.

DETAILED DESCRIPTION OF THE INVENTION

This invention relates to a synthetic method for the production of terbinafine and analogues thereof, including the step of reacting the compound of general formula (6):

(6)

with the compound of general formula (7):

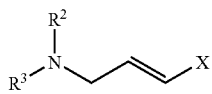
(7)

to give the product of general formula (8):

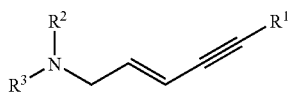
(8)

in the presence of a metal catalyst, wherein $R^1$ is selected from: linear or branched $(C_{1-10})$ alkyl; linear or branched $(C_{1-10}$ alkenyl; linear or branched $(C_{1-10}$ alkynyl; $(C_{3-7})$ cycloalkyl; $(C_{4-7})$ cycloalkenyl; aryl $(C_{0-4})$alkyl, either substituted or unsubstituted in any position, with linear or branched $(C_{1-6})$ alkyl, linear or branched $(C_{1-6})$ alkenyl, linear or branched $(C_{1-6})$ alkynyl, $(C_{1-6})$ alkoxy, nitro, trifluoromethyl, a tertiary amino group; a naphthyl $(C_{0-4})$ alkyl either substituted or unsubstituted, in any position, with linear or branched $(C_{1-6})$ alkyl; linear or branched $(C_{1-6})$ alkenyl; linear or branched $(C_{1-6})$ alkynyl, $(C_{1-6})$ alkoxy, nitro, trifluoromethyl, a tertiary amino group; or is a heterocycle selected from: unsubstituted pyridine, pyrimidine, pyrazine, pyridazine, quinoline, isoquinolin, furan, benzofuran, thiazole, isothiazole, oxazole and isoxazole. Preferably, $R^1$ is: linear or branched $(C_{1-10})$ alkyl; linear or branched $(C_{1-10})$ alkenyl; linear or branched $(C_{1-10})$ alkynyl; $(C_{3-7})$ cycloalkyl; $(C_{4-7})$ cycloalkenyl; aryl $(C_{0-4})$ alkyl, either substituted or unsubstituted, in any position, with linear or branched $(C_{1-6})$ alkyl, linear or branched $(C_{1-6})$ alkenyl, linear or branched $(C_{1-6})$ alkynyl, $(C_{1-6})$ alkoxy, nitro, trifluoromethyl or a tertiary amino group.

More preferably, it is a linear or branched $(C_{1-10})$ alkyl group.

$R^2$ is selected from: linear or branched $(C_{1-10})$ alkyl; linear or branched $(C_{1-10})$ alkenyl; linear or branched $(C_{1-10})$ alkynyl; $(C_{3-7})$ cycloalkyl; $(C_{4-7})$ cycloalkenyl; aryl $(C_{0-4})$ alkyl, either substituted or unsubstituted in any position, with linear or branched $(C_{1-6})$ alkyl, linear or branched $(C_{1-6})$ alkenyl, linear or branched $(C_{1-6})$ alkynyl, $(C_{1-6})$ alkoxy, nitro, cyano, halo, trifluoromethyl, a tertiary amino group; or is a naphthyl $(C_{0-4})$ alkyl either substituted or unsubstituted, in any position, with linear or branched $(C_{1-6})$ alkyl; linear or branched $(C_{1-6})$ alkenyl; linear or branched $(C_{1-6})$ alkynyl, $(C_{1-6})$ alkoxy, nitro, cyano, halo, trifluoromethyl, a tertiary amino group; or is a heterocycle selected from: pyridine, pyrimidine, pyrazine, pyridazine, quinoline, isoquinoline, furan, benzofuran, thiazole, isothiazole, oxazole, isoxazole, either substituted or unsubstituted with linear or branched $(C_{1-6})$ alkyl, linear or branched $(C_{1-6})$ alkenyl, linear or branched $(C_{1-6})$ alkynyl, $(C_{1-6})$ alkoxy, nitro, cyano, halo, trifluoromethyl or a tertiary amino group.

Preferably, $R^2$ is: linear or branched $(C_{1-10})$ alkyl; linear or branched $(C_{1-10})$ alkenyl; linear or branched $(C_{1-10})$ alkynyl; $(C_{3-7})$ cycloalkyl; $(C_{4-7})$ cycloalkenyl; aryl$(C_{0-4})$ alkyl, either substituted or unsubstituted, in any position, with linear or branched $(C_{1-6})$ alkyl, linear or branched $(C_{1-6})$ alkenyl, linear or branched $(C_{1-6})$ alkynyl, $(C_{1-6})$ alkoxy, nitro, cyano, halo, trifluoromethyl or a tertiary amino group.

More preferably, it is a linear or branched $(C_{1-10})$ alkyl group.

$R^3$ is selected from: hydrogen, linear or branched $(C_{1-10})$ alkyl; linear or branched $(C_{1-10})$ alkenyl; linear or branched $(C_{1-10})$ alkynyl; $(C_{3-7})$ cycloalkyl; $(C_{4-7})$ cycloalkenyl; aryl $(C_{0-4})$ alkyl, either substituted or unsubstituted in any position, with linear or branched $(C_{1-6})$ alkyl, linear or branched $(C_{1-6})$ alkenyl, linear or branched $(C_{1-6})$ alkynyl, $(C_{1-6})$ alkoxy, nitro, cyano, halo, trifluoromethyl, a tertiary amino group; a naphthyl $(C_{0-4})$ alkyl either substituted or unsubstituted, in any position, with linear or branched $(C_{1-6})$ alkyl; linear or branched $(C_{1-6})$ alkenyl; linear or branched $(C_{1-6})$ alkynyl, $(C_{1-6})$ alkoxy, nitro, cyano, halo, trifluoromethyl; a tertiary amino group; a heterocycle selected from: pyridine, pyrimidine, pyrazine, pyridazine, quinoline, isoquinoline, furan, benzofuran, thiazole, isothiazole, oxazole, isoxazole, either substituted or unsubstituted with linear or branched $(C_{1-6})$ alkyl, linear or branched $(C_{1-6})$ alkenyl, linear or branched $(C_{1-6})$ alkynyl, $(C_{1-6})$ alkoxy, nitro, cyano, halo, trifluoromethyl, a tertiary amino group; or is a $Si(R^4)_3$ group wherein $R^4$ is a linear or branched $(C_{1-5})$ alkyl group or an unsubstituted aryl $(C_{0-4})$alkyl group.

Preferably, $R^3$ is: a naphthyl $(C_{0-4})$ alkyl, either substituted or unsubstituted in any position with linear or branched $(C_{1-6})$ alkyl, linear or branched $(C_{1-6})$ alkenyl, linear or branched $(C_{1-6})$ alkynyl, $(C_{1-6})$ alkoxy, nitro, cyano, halo, trifluoromethyl, a tertiary amino group; or is an $Si(R^4)_3$ group, wherein $R^4$ is a linear or branched $(C_{1-5})$ alkyl group. Even more preferably, $R^3$ is an unsubstituted naphthyl $(C_{0-4})$ alkyl group or is an $Si(R^4)_3$ group, wherein $R^4$ is a linear $(C_{1-5})$ alkyl group.

X is chlorine, bromine, iodine or fluorine, preferably it is either chlorine or bromine. More preferably, it is chlorine.

Even more preferably, $R^1$ is a tert-butyl group, $R^2$ is a methyl group and $R^3$ is an α-naphthylmethyl group i.e. the product of general formula (8) is terbinafine.

The metal catalyst may be selected from salts or complexes of Ni, Pd, Cu, Fe, Sn, Zn and Ti. Preferably, the metal catalyst is a Ni and Pd salt or complex. Even more preferably, it is a Ni(II) complex or salt.

Examples of Ni(II) salts include: nickel chloride, nickel bromide, nickel iodide, nickel fluoride, nickel sulphate, nickel nitrate, nickel acetate, nickel acetylacetonate and nickel oxide. The preferred salt is nickel chloride.

Examples of Ni(II) complexes include:

[1,2-bis(diphenylphosphino)ethane]dichloro nickel(II);

[1,1-bis(diphenylphosphino)ferrocene]dichloro nickel(II);

[1,3-bis(diphenylphosphino)propane]dichloro nickel(II);

dibromo bis(tributylphosphine) nickel(II);

dibromo bis(triphenylphosphine) nickel(II);

dichloro bis(tributylphosphine) nickel(II);

dichloro bis(trimethylphosphine) nickel(II);

dichloro bis(triphenylphosphine) nickel(II);

The preferred complex is dichloro bis (triphenylphosphine) nickel(II).

The nickel salts and complexes may also be used as mixtures thereof.

Particularly preferred amongst all the Ni catalysts is $NiCl_2$ which emerged as being better with respect to dichloro bis (triphenylphosphine) nickel(II), allowing the reaction to be carried out under milder conditions and for shorter periods of time.

The compound of formula (6), in the case where $R^1$ is a radical capable of forming a sufficiently stable carbocation, may be synthesised using the methodology reported below:

Scheme 2

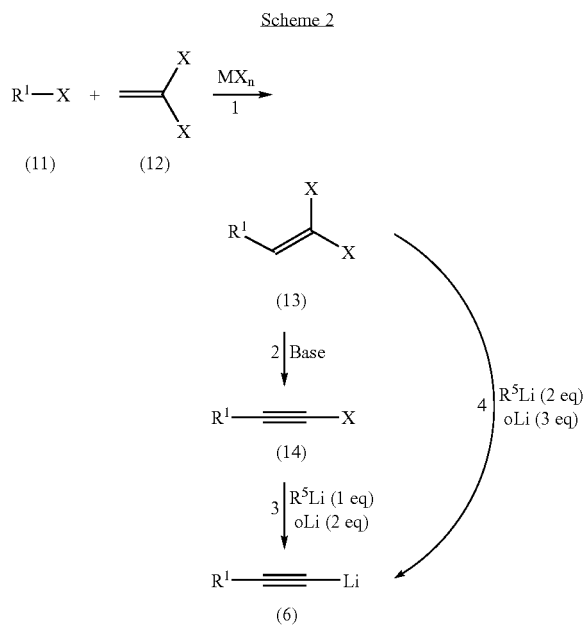

$MX_n$ (with n=2, 3, 4) are Lewis acids wherein X is a halogen, preferably chlorine or bromine, even more preferably chlorine;

M is selected from: iron, aluminium, zinc, tin, boron and titanium. Preferably, M is iron or aluminium; even more preferably M is iron.

The above Lewis acid is used in catalytic amounts together with a solvent selected from either chlorinated solvents, particularly methylene chloride and 1,2,4-trichlorobenzene, or nitro-organic compounds, particularly nitrobenzene or mixtures thereof.

The use of high boiling point solvents (boiling points in excess of 100° C.) is particularly preferable since the relative vapour pressure for the two reagents (11) and (12) is reduced, thus limiting their evaporation during the reaction.

The preferred reaction method consists in the addition of a solution of reagents (11) and (12) to a suspension or solution of $MX_n$ in one or more of the above mentioned solvents at a temperature within the range 10-40° C. and preferably between 20° and 25° C. Product (13) may be easily isolated by fractional distillation, either directly from the reaction mixture, or following a normal aqueous work-up, with yields from 50 to 90 molar percent, preferably from 55 to 60 molar percent and purity from 80 to 99%, preferably from 96 to 98%.

Step 2, in scheme 2, is conveniently carried out using an inorganic base, such as for example potassium or sodium hydroxide, sodium or potassium carbonate, preferably NaOH or KOH, in a polar solvent with a high boiling point, such as for example ethylene glycol, propylene glycol, diethylene glycol, diglyme, dimethylsulphoxide, N-methylpyrrolidone, dimethylformamide, dimethylacetamide, preferably ethylene glycol, and by distillation of the product directly from the reaction mixture.

The product (14) is subsequently reacted with an organolithium base (step 3) $R^5Li$, wherein $R^5$ is methyl, n-butyl, sec-butyl, tert-butyl, n-hexyl, cyclohexyl, phenyl, preferably n-butyl, or rather directly with metallic lithium to give product (6) with quantitative yield.

Alternatively, compound (14) may be converted directly into product (6) (step 4), by reacting with two moles of an organolithium base ($R^5Li$) or else directly with metallic lithium.

In the first case, the reaction may be performed directly in non-polar solvents such as toluene or heptane at a temperature of between 20° and 110° C. and preferably within the range 70-90° C.; instead, in the second case it is necessary to use an ethereal solvent, from amongst which, tetrahydrofuran is preferred. The most preferred is the reaction which provides step 4.

In the case where an organolithium base is used, it is preferable to remove the corresponding alkyl halide w2hich forms in the reaction by distillation, prior to performing the subsequent coupling reaction.

The overall outline for the preparation of compound (6) is described in the following publications: H. G. Viehe and S. Y. Delavarenne, Chem. Ber. 103, 1216-1224 (1970) and Z. Wang et al. *Tetr. Lett.* 41 (2000), 4007-4009.

However, the methods reported in the above documents are characterised by low industrial applicability. The optimisation introduced by the present invention, especially with regard to step 1, has provided a synthetic methodology allowing the attainment of product (6) under milder conditions and with higher yield. These and further advantages of the use of reaction outline 2 will be discussed below.

It is understood that reagent (6) may also be obtained by using synthetic methodologies other than that illustrated without departing from the scope of protection of the present invention.

In cases where $R^3$ is a $Si(R^4)_3$ group, wherein $R^4$ is as described above, reagent (7) may be obtained according to the following synthetic scheme:

Scheme 3

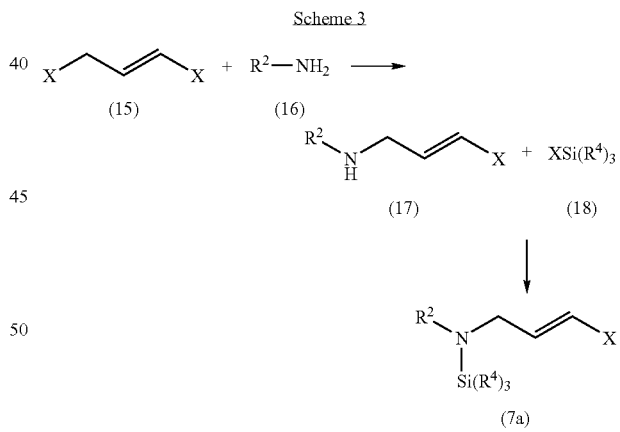

The most convenient process involves the addition of compound (15) to an aqueous amine mixture (14) in molar excess, and a non-polar organic solvent, such as for example heptane, hexane, pentane, cyclohexane, toluene, xylene, mesithylene or mixtures thereof, preferably heptane, at a temperature of between 0° and 100° C., preferably between 15° and 25° C., for a period of time of 0.5 to 5 hours, preferably of 1 to 3 hours. That way, it is possible to minimise formation of the dialkylation by-product, which remains more or less quantitatively in the non-polar solvent at the end of the reaction, whilst compound (17) remains in the aqueous moiety and may be subsequently extracted with a polar solvent, such as for example methyl tert-butyl ether, methylene chloride, ethyl acetate, diethyl ether, preferably methyl tert-butyl ether or methylene chloride. Product (17) is purified by distillation, but, not being particularly stable, it has been more convenient to use the product in crude form, or by performing the isolation of the corresponding hydrochloride salt, obtained through the addition of hydrochloric acid directly into the final solution in an organic solvent.

The nitrogen group on the intermediate of formula (17) may conveniently be protected by reacting with compound (18) in the presence of an organic base, such as for example triethylamine, trimethylamine, N-ethyl-di-isopropylamine, diazabicyclononane (DBN), diazabicycloundecene (DBU), preferably triethylamine, in an inert solvent, such as for example toluene, methyl tert-butyl ether, di-isopropyl ether, methylene chloride, ethyl acetate, isopropyl acetate, preferably toluene, in order to give product (7a).

The protection reaction takes place under very mild conditions at temperatures within the range 0°-50° C. and preferably within the range 20°-30° C. and is complete within a few hours.

The work-up provides the filtration of the chloride from the used organic base (for example triethylamonium chloride) and concentration to a small volume under vacuum with the aim of eliminating any possible excess of compound (18).

The product of general formula (7a) is subsequently reacted in situ with the suspension of product (6) in a solvent such as THF, dioxan, glyme, diglyme, dimethoxyethane, diethoxyethane, toluene, xylene, preferably in a THF/toluene mixture, with a suitable catalyst (nickel salts or complexes or mixtures thereof) and then heating the reaction mixture to a temperature within the range 50-100° C. and preferably between 70° and 95° C.; the reaction is complete and quantitative within 0.5-10 hours, preferably 1-4 hours. Thus, product (8a) is obtained, wherein $R^3$ is a $Si(R^4)_3$ group and $R^1$, $R^2$ and $R^4$ are as defined above. Following this synthetic route, product (8a) must be subsequently modified according to the following scheme:

Scheme 4

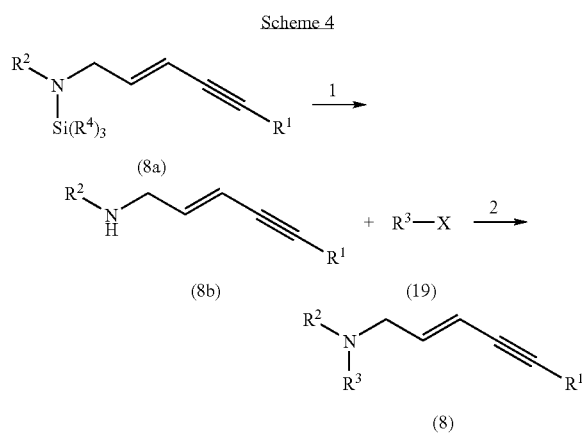

in order to obtain the final product (8) wherein $R^1$, $R^2$, $R^3$ are as defined above.

In particular, compound (8a) may be subjected to a simple aqueous work-up, optionally in the presence of acids or bases, (step 1 in outline 4) in order to obtain the de-protected product (8b) which may be used as crude product or isolated by distillation or by the crystallisation of a suitable organic or inorganic salt thereof (for example as the hydrochloride, hydrobromide, citrate, oxalate, succinate or tartrate salt). The latter may be easily alkylated with product (19) (step 2) in a ketone solvent (for example: acetone, methyl ethyl ketone, methyl isobutyl ketone, cyclohexanone) or aprotic polar solvent (for example: dimethylformamide, dimethylacetamide, N-methylpyrrolidone, Dimethylsulphoxide) and in the presence of a suitable base, such as sodium or potassium hydroxide, sodium or potassium carbonate, sodium or potassium acetate, in order to trap the hydrochloric acid produced.

The crude final product (8) is obtained by the separation of the aqueous phase and concentration of the solvent to residue. Preferably, compound (8) is isolated from the crude mixture in hydrochloride form.

The crude product is dissolved in a solvent such as methyl ethyl ketone, acetone, isopropyl acetate, isopropanol, toluene, preferably isopropanol, methyl ethyl ketone, more preferably methyl ethyl ketone; then HCl is added and precipitation of the product hydrochloride is obtained (8). Separation from the solvent occurs according to techniques known in the art, for example by filtration.

One preferred application consists in heating a mixture of (8b) and (19) in toluene, with an aqueous solution of sodium hydroxide, optionally in the presence of a phase transfer catalyst, such as for example tetrabutylammonium bromide, tetrabutylammonium bisulphate, tetrabutylammonium hydroxide, cetyltrimethylammonium chloride, preferably tetrabutylamonium bromide, at a temperature of between 50 and 100° C., preferably between 70° and 90° C. for a period of time of 1 to 10 hours, preferably 4-6 hours. The reaction is quantitative and the crude product (8) is obtained simply by separation of the aqueous phase and concentration of solvent to residue. However, it has been surprisingly found that isolation of intermediate (8b) is not in fact necessary, in that product (8a) may be reacted directly with compound (19), according to the previously described process, so as to directly give the crude final product (8). Indeed, given the relative instability of compounds of this type:

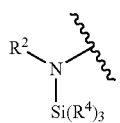

the alkylation reaction conditions are sufficient to destroy the $Si(R^4)_3$ group, with the in situ formation of the intermediate (8b) which reacts immediately with compound (19) to give the final product (8).

This final embodiment is the most preferred since it allows the attainment of final product (8) starting from compounds (15) and (16), with a practically "one pot" process. Using this method, product (8) is preferably obtained in the hydrochloride form, with an overall yield of 40-80 molar percent, preferably 50-65 molar percent with purity from 95 to 100%, preferably in excess of 99%.

When $R^3$ is other than $Si(R^4)_3$, then product (7) may be obtained according to the following reaction scheme:

Scheme 5

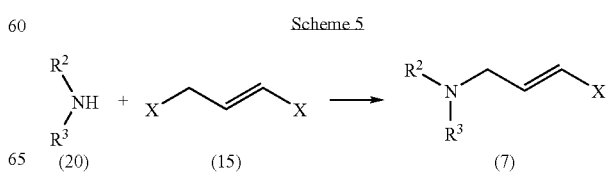

reported in patents EP 0 421 302 and EP 0 645 369. Product (7) is used, without purification, in the subsequent coupling step with compound (6) following the same aforementioned methods, thus directly giving the final product (8). Again, in this case, the preparation of (8) is practically "one-pot", starting from reagents (20) and (15).

Work-up of the reaction provides an initial treatment with an aqueous solution of a Ni complexing agent, for example, an aqueous solution of EDTA, ammonia, ethylene diamine, tetramethylethylene diamine, preferably an aqueous solution of ammonia, in order to remove it from the organic phase; a subsequent wash with water and then concentration of the remaining organic phase to residue allows attainment of the crude product (8) with quantitative yield and purity from 60 to 95%, preferably from 70% to 90% (HPLC).

Preferably, compound (8) is isolated in hydrochloride form by the addition of hydrochloric acid to the solution of crude product dissolved in an appropriate organic solvent, such as for example acetone, methyl ethyl ketone, isopropanol, ethyl acetate, isopropyl acetate or toluene; the resulting precipitate in then isolated by filtration.

The overall yield of this process, as product (8) in hydrochloride form, is between 50 and 90 molar percent, preferably between 60 and 70 molar percent, and the product thus obtained has a purity of between 95 and 100%, preferably in excess of 99% (HPLC, A %—percentage peak area from HPLC analysis).

Obviously, product (7) may also be obtained through other synthetic methods without departing from the scope of protection of the present invention.

ADVANTAGES

The method currently most used for the synthesis of terbinafine is reported in scheme 1. This synthetic process is brief, simple to perform and gives good yield, however, it uses tert-butylacetylene and palladium catalysts which are both very expensive compounds. This all has an influence over the final price of the drug, with obvious social consequences. The present invention provides two linked, equally valid synthetic routes which allow the attainment of terbinafine and derivatives thereof, in a way which is more economical and more suited to industrial application.

The key step is the reaction between compound (6), easily synthesised and much more economical than tert-butylacetylene, and compound (7), obtainable through rapid and economical synthetic routes. The use of very economical Ni catalysts, especially Ni salts, and compound (6) allow a drastic reduction in the total production costs for terbinafine and derivatives thereof. Furthermore, the coupling reaction may be carried out under much milder conditions and for much shorter times.

Compound (6) is obtained through a synthetic route (scheme 2) reported in the literature, which has been selected since it uses very economical starting materials (11) and (12). This method has been optimised in the present invention, thus providing a method characterised by improved industrial applicability. The use of $AlCl_3$ as a Lewis acid in step 1 has indeed been reported in the literature. As shown experimentally, the use of aluminium chloride in this reaction causes uncontrolled HCl production and significant foaming, making it unsuitable for large scale industrial use. Instead, according to the present invention, the use of a weaker Lewis acid (for example $FeCl_3$), and different methods for the addition of the reagents, together with the use of a high boiling point solvent, allows the attainment of more controllable reaction conditions. More conveniently, compound (13) may be treated directly with an organolithium base or with metallic Li (step 4) thus shortening reaction times.

Compound (7) may be obtained using the method reported in scheme 5, already published in the literature. Conveniently, in this case, the final product (8) is obtained not only by using an economical and industrially applicable method, but also by using an essentially "one-pot" process, and hence much more rapid.

Indeed, the only purification step performed throughout this synthetic route is that of the final product.

Alternatively, compound (7a) may be obtained by starting from the very economical reagents (15) and (16), using the process outlined in schemes 3 and 4, which is practically "one-pot", and hence very rapid. Again, in this case, the only product to be purified is the final product.

Hence, in summary, the present invention provides a process for the synthesis of terbinafine and analogues thereof, characterised by good industrial applicability, good process speed and ease of execution and a yield comparable with the processes of the known art. Above all, it provides a method which is much more economical than the known art, which is reflected in a significant reduction in the final cost of the drug.

EXPERIMENTAL SECTION

Example 1

1,1-dichloro-3,3-dimethylbutene

Into a reactor in an inert atmosphere are introduced 50.0 g (0.3 mol) of $FeCl_3$ and 350 ml methylene chloride. To this suspension, at a temperature of 20-25° C., a mixture consisting of 478 ml (407 g; 4.39 mol) tert-butyl chloride and 380 ml (426 g; 4.39 mol) vinylidene chloride is added dropwise over a period of 3 hours. Half-way through the addition of the solution are added 20 g (0.123 mol) of $FeCl_3$ with the addition of a further 5 g (0.07 mol) at the end. The reaction mixture is then left stirring for two hours and the suspension poured into a reactor containing 500 ml water. The phases are separated and the organic phase washed with 250 ml water and subsequently with 250 ml of a 5% w/w aqueous solution of $NaHCO_3$.

The organic phase is distilled under vacuum to give 395 g (2.58 mol-58% yield) of 1,1-dichloro-3,3-dimethylbutene (a fraction which distils at P=140 mbar; T=65° C.) with a purity of 95.1% GC (A %)—(percentage peak area from GC analysis).

Example 2

1,1-dichloro-3,3-dimethylbutene

Into a reactor in an inert atmosphere are introduced 50.0 g (0.3 mol) of $FeCl_3$ and 350 ml 1,2,4-trichlorobenzene. To this suspension, at a temperature of 20-25° C., a solution consisting of 478 ml (407 g; 4.39 mol) tert-butyl chloride and 380 ml (426 g; 4.39 mol) vinylidene chloride is added dropwise over a period of 4 hours, and the mixture left stirring for 16 hours. The suspension is then poured into a reactor containing 500 ml water. The phases are separated and the organic phase washed with 250 ml water and subsequently with 250 ml a 5% w/w aqueous solution of $NaHCO_3$.

The organic phase is distilled to give 387 g (2.53 mol-57.6% yield) 1,1-dichloro-3,3-dimethylbutene (a fraction which distils at P=100 mbar; T=65° C.) with a purity of 93.0% GC (A %).

Example 3

1,1-dichloro-3,3-dimethylbutene 25.0 g (0.15 mol) $FeCl_3$ and 175 ml nitrobenzene are introduced into a reactor under inert atmosphere.

To this solution, a mixture consisting of 239 ml (204 g; 2.2 mol) tert-butyl chloride and 190 ml (213 g; 2.2 mol) vinylidene chloride at a temperature of 20-25° C. is added dropwise over a period of 2 hours, and the mixture left stirring for two hours.

The mixture is distilled under vacuum thus collecting a fraction of 150 g (0.98 mol-41% yield) of 1,1-dichloro-3,3-dimethylbutene (a fraction which distils at P=140 mbar; T=65° C.) with a purity of 94.4% GC (A %).

Example 4 tert-butyl-2-chloro-acetylene 180 g (3.2 mol) KOH pellets and 300 ml diethylene glycol are introduced into a reactor. The reaction mixture is heated to 90° C. and having reached said temperature, 110 g (0.719 mol) 1,1-dichloro-3,3-dimethylbutene is added over the period of an hour. The mixture is stirred at 90° C. for 3 hours and then the product distilled at atmospheric pressure with a reactor internal temperature of 95° C., thus giving a mixture of the product and water, formed as a reaction by-product, which is then separated. The product is dried over anhydrous $Na_2SO_4$, to give 70.0 g (84% yield) of the desired compound as a colourless liquid, with a purity of 98.8% GC (A %).

Example 5

N-(trans-3-chloro-2-propenyl)-N-methyl-1-naphthalene-methanamine 30 g (0.175 mol) N-methyl-1-naphthalene methanamine, 100 ml MEK and 29 g (0.210 mol, 1.2 eq.) potassium carbonate are introduced into a reactor, the mixture is heated to 50° C. and 22.4 g (0.202 mol, 1.1 eq.) of (1E)-1,3-dichloro-1-propene added dropwise.

Upon complete addition, the mixture is heated at 80°/85° C., and the reaction is complete after 7 hours, the mixture is distilled to a small volume, cooled and 120 ml toluene and 150 ml water added. The phases are separated and the aqueous phase extracted with 2×45 ml toluene and the combined organic phases washed with 2×60 ml water. This is then concentrated to a residue to give 41.5 g (0.168 mol, 96.5% yield) of product, as a reddish-yellow oil, with 92.0% purity (HPLC A %).

Example 6

Terbinafine (1)

50.0 g (0.321 mol) of dimethylbutene and 250 ml toluene are introduced into a reactor. The resulting solution is heated at 80° C., and then 242.5 ml 25% n-butyllithium (2.1 eq.) in heptane is added over a period of 45 minutes at 80-90° C. Upon complete addition, the resulting white suspension is stirred for 2 hours at 80° C. A mixture of toluene, heptane and chlorobutane, reaction by-product, is then subsequently distilled at atmospheric pressure under a flow of nitrogen, at the same time adding toluene in order to keep the initial volume constant.

The suspension is cooled to 80° C. and 66.7 g (0.247 mol, 0.8 eq., titre HPLC A % 91.0%), of crude N-(trans-3-chloro-2-propenyl)-N-methyl-1-naphthalenemethanamine, 100 ml THF and 480 mg $NiCl_2$ (3.7 mmol, 0.011 eq.) added.

The reaction mixture is heated at 90°-95° C. for 1 hour and then cooled to 20-25° C. 400 ml water and 100 ml of 30% aqueous ammonia are added; the phases are separated and the aqueous phase re-extracted with 250 ml toluene. The combined organic phases are washed with 2×250 ml water and subsequently treated with 3.5 g of acticarbon. After stirring for 30 minutes at 20/25° C., the carbon is filtered, washing the filter with 100 ml toluene. The organic phase is concentrated to residue, thus giving 62.8 g (0.215 mol, 87.0% yield) of crude terbinafine, with a purity of 87.3% HPLC A.

Example 7

Terbinafine (1)

10.0 g (0.06 mol) 1,1-dichloro-3,3-dimethylbutene and 50 ml toluene are introduced into a reactor. The resulting solution is heated at 80° C., and then 45.5 ml 25% n-butyllithium (2.1 eq.) in heptane are added over a period of 30 minutes. Upon complete addition, the resulting white suspension is stirred for 2 hours at 80° C. A mixture of toluene and chlorobutane, reaction by-product, is then subsequently distilled at atmospheric pressure under a flow of nitrogen, at the same time adding toluene in order to keep the initial volume constant.

The suspension is cooled to 50° C. and 10.8 g (0.04 mol, 0.66 eq.) of crude N-(trans-3-chloro-2-propenyl)-N-methyl-1-naphthalenemethanamine, 20 ml THF, 52 mg $NiCl_2$ (0.7 molar percent) and 210 mg triphenylphosphine added.

The reaction mixture is heated at 90°-95° C. for 4 hours.

The mixture is cooled and, at 20°/25° C., 100 ml of a 2.5% aqueous EDTA disodium salt solution added, the phases are separated and the aqueous phase re-extracted with 75 ml toluene. Finally, the combined organic phases are washed with 2×80 ml water. The organic phase is concentrated to residue, thus giving 15.1 g (in excess of theoretical yield) crude terbinafine, with a purity of 76.4% (HPLC A %).

Example 8

Terbinafine (1)

The reaction described in example 6 is repeated, using 421 mg $PdCl_2(PPh_3)$ (1.4 mol %) as a catalyst. The reaction mixture is heated at 90°-95° C. for 4 hours and subsequently cooled to 20-25° C. Following the work-up described in example 6, 14.2 g (greater than the theoretical yield), of crude terbinafine are obtained, with purity of 81.7% (HPLC A %).

Example 9

Terbinafine (1)

10.0 g (0.0858 mol) tert-butyl-2-chloro-acetylene and 50 ml toluene are introduced into a reactor. The resulting solution is heated at 80° C., and then over a period of 30 minutes, 35.5 ml of 25% n-butyllithium (1.15 eq.) in heptane are added.

Upon complete addition, the resulting white suspension is stirred for 2 hours at 80° C. A mixture of toluene and chlorobutane, reaction by-product, is then subsequently distilled at atmospheric pressure under a flow of nitrogen, at the same time adding toluene in order to keep the initial volume constant.

The mixture is cooled to 50° C. and 15.5 g (0.0572 mol) crude N-(trans-3-chloro-2-propenyl)-N-methyl-1-naphthalene-methylamine, 20 ml THF and 74 mg NiCl$_2$ (0.77 molar percent) introduced. The reaction mixture is heated at 90°-95° C. for 1 hour, cooled to 20°/25° C. and 130 ml of a 2.5% (w/v) aqueous solution of EDTA disodium salt added, the phases are separated and the aqueous phase re-extracted with 70 ml chilled toluene. The combined organic phases are washed with 2×90 ml water and concentrated to a residue, thus giving 18.2 g (greater than theoretical yield) terbinafine with a purity of 83.6% (HPLC A %).

Example 10

Terbinafine (1)

The reaction described in example 9 is repeated, using 600 mg of PdCl$_2$(PPh$_3$) (1.4 molar percent) as a catalyst. The reaction mixture is heated at 90°-95° C. for 1 hour and subsequently cooled to 20-25° C. Following the work-up described in example 8, 19.2 g (greater than the of terbinafine base are obtained, with purity of 80.4% (HPLC A %).

Example 11

Terbinafine (1)

The reaction described in example 9 is repeated, using a mixture of 77 mg of NiCl$_2$ (0.7% mol) and 300 mg of triphenylphosphine as a catalyst. The reaction mixture is heated at 90°-95° C. for 1 hour.

Following the work-up described in example 8, 19.2 g (greater than theoretical yield) of terbinafine are obtained with a purity of 74.4% (HPLC A %).

Example 12

Terbinafine (1)

Into a reactor in an inert atmosphere are introduced 1.58 g (0.228 mol) of lithium granules and 40 ml tetrahydrofuran. The suspension is heated at 50° C. and subsequently a solution consisting of 10 g (0.065 mol) 1,1-dichloro-3,3-dimethylbutene 5 and 10 ml THF added dropwise over a period of 40 minutes.

The reaction mixture is refluxed for three hours until the complete consumption of the reagent. Then 10.6 g (0.043 mol) crude N-(trans-3-chloro-2-propenyl)-N-methyl-1-naphthalene-methanamine, 80 mg (0.61 mmol) NiCl$_2$ and 10 ml THF are added. The mixture is kept refluxing for 6 hours and then cooled to 20° C.

10 ml water, 50 ml of a 5% (w/v) solution of EDTA disodium salt and 50 ml toluene are added to the reaction mixture. The suspension is stirred and the phases separated.

The organic phase is washed with 3×50 ml of a 5% EDTA solution adjusted to pH 9 with NH$_4$OH and finally, concentrated to residue to give 12.5 g of crude terbinafine (greater than theoretical yield) with a purity of 64.4%.

Example 13

Terbinafine (1)

1.5 g (0.216 mol) lithium granules which are then covered with 40 ml tetrahydrofuran are introduced into an inertised reactor. The suspension is heated to 50° C. and subsequently a solution consisting of 10 g (0.085 mol) tert-butyl-2-chloroacetylene and 10 ml THF is added dropwise over a period of 40 minutes. The reaction mixture is refluxed for two hours until the complete consumption of the reagent.

110 mg (0.085 mmol) NiCl$_2$, 10 ml THF and 13.9 g (0.0566 mol, 0.66 eq.) crude N-(trans-3-chloro-2-propenyl)-N-methyl-1-naphthalenemethanamine are introduced into an inertised reactor under nitrogen; the suspension is then poured into the reactor mentioned above.

The mixture is refluxed for 5 hours, after which time, it is cooled to room temperature and then 10 ml water, 50 ml of a 5% aqueous EDTA solution and 50 ml toluene are added.

The suspension is stirred and the phases separated. The organic phase is washed a further three times with 50 ml of a 5%; EDTA solution adjusted to pH 9 with NH$_4$OH and finally, concentrated to residue to give 17.5 g of crude terbinafine (greater than theoretical yield) with a purity of 65.5%.

Example 14

Terbinafine (1)

1.5 g (0.216 mol) lithium granules which are then covered with 40 ml tetrahydrofuran are introduced into an inertised reactor. The suspension is heated to 50° C. and subsequently a solution consisting of 10 g (0.085 mol) tert-butyl-2-chloroacetylene and 10 ml THF is added dropwise over a period of 40 minutes. The reaction mixture is refluxed for two hours until the complete consumption of the reagent.

110 mg (0.085 mmol) NiCl$_2$, 455 mg triphenylphosphine and 10 ml THF are introduced into a second inertised reactor under nitrogen.

The mixture is heated until a yellow precipitate is obtained, then 13.9 g (0.0566 mol) crude N-(trans-3-chloro-2-propenyl)-N-methyl-1-naphthalenemethanamine are added.

The resulting suspension is poured into the first reactor and the mixture refluxed for 2 hours until complete conversion, and then cooled to room temperature.

By following the same work-up as example 13, 17.0 g (greater than theoretical yield) crude Terbinafine is obtained with a purity of 74.5%.

Example 15

Terbinafine (1) hydrochloride 14.1 g crude terbinafine (39.9 mmol theoretical, example 6) is dissolved in 94 ml methyl ethyl ketone (MEK) and then 3.9 ml (0.0399 mol) of 32% aqueous hydrochloric acid is added dropwise. The resulting suspension is stirred for 30 minutes and then concentrated to a small volume, using a rotavapor to azeotropically distil off the water. The initial volume is restored with chilled MEK. After stirring for 2 hours at 20° C., the precipitate is filtered, washed with 2×11 ml MEK and dried to constant weight under a heat lamp. 8.7 g (66.4% yield) of terbinafine-HCl are obtained as a white solid with purity of 99.3% (HPLC A %).

Example 16

Terbinafine (1) hydrochloride 14.2 g crude terbinafine base (40.0 mmol theoretical, example 6) is dissolved in 24 ml isopropanol and then 17.2 g (1.1 eq.) of 9.35% hydrochloric acid in isopropanol are added dropwise.

The resulting solution is stirred for 30 minutes, then concentrated to a small volume using a rotavapor, and then taken up with 24 ml chilled isopropanol.

71 ml diisopropyl ether is then added dropwise at 20/25° C.; the crystallisation of the product is observed following the addition of approx. half of the amount of ether.

Following stirring for 8 hours at 20° C., the precipitate is filtered, washed with 2×14 ml of an iPrOH/diisopropyl ether mixture (⅓ by volume) and dried to constant weight at 40° C. in a vacuum oven. 8.3 g (63% yield) terbinafine-HCl is obtained as a white solid with purity of 95.0% (HPLC A %).

Example 17

Terbinafine (1) hydrochloride 19.2 g crude terbinafine base (57.2 mmol theoretical, example 6) is dissolved in 83 ml acetone and then 6.2 ml (0.0631 mol) of 32% aqueous hydrochloric acid is added dropwise. The resulting suspension is stirred for 30 minutes at 20° C. and then cooled to −5°/−10° C. and stirred for a further 2.5 hours. The precipitate is filtered, washed with 16 ml cold acetone and dried to constant weight at 40° C. in a vacuum oven. 10.8 g (57.5% yield) terbinafine-HCl is obtained as a white solid with purity in excess of 99.8% (HPLC A %).

Example 18

Terbinafine (1) hydrochloride 17.6 g crude terbinafine base (56.6 mmol theoretical, example 13) is dissolved in 80 ml (4.5 vol.) of acetone and 6.8 ml (1.1 eq.) of 32% aqueous hydrochloric acid are added.

The resulting suspension is cooled to −20° C. and stirred for 2 hours. The precipitate is filtered, washed with 20 ml acetone and dried at 40° C. in a vacuum oven to give 4.9 g (29.7% yield) of Terbinafine hydrochloride as a white solid with purity in excess of 99.9% (HPLC A %).

Example 19 trans-1-methylamine-3-chloro-2-propene hydrochloride 700 ml (7.9 mol 8.8 eq.) of 40% aqueous methylamine is introduced into a 2 liter reactor, and a 100 g solution (0.9 mol) of 1,3-dichloropropene (E isomer) dissolved in ml heptane are added dropwise at 20-25° C. The suspension is kept stirring for 3 hours and then the two phases are separated. The aqueous phase is washed with 25 ml heptane and the combined organic phases are extracted with 50 ml of a 5% aqueous solution of $NH_4Cl$.

The combined aqueous phases are extracted 5 times with a total of 600 ml MTBE. The organic phases are concentrated by the distillation of 500 ml solvent under vacuum and then restored to 200 ml with MTBE. Gaseous HCl is bubbled through until a pH≈2 is achieved, and the suspension thus obtained is stirred at 20° C. for 2 hours.

The precipitate is then filtered using a Buchner funnel, washed with 50 ml MTBE and dried under vacuum at 40° C., to give 77.5 g product (60.6% yield), with purity of 99.0% (GC, A %).

Example 20

N-trimethylsilyl-trans-1-methylamino-3-chloro-2-propene

Into a reactor under an inert nitrogen atmosphere are introduced 80 g (0.56 mol) trans-1-methylamino-3-chloro-2-propene hydrochloride, 400 ml toluene, 160 ml 25% NaOH and the mixture is stirred for 20 minutes at 20-25° C. The organic phase is separated and the aqueous phase extracted with 100 ml toluene. To the combined organic phases are added 150 ml triethylamine (1.07 mol, 1.9 eq.) and 98 ml trimethylchlorosilane (0.77 mol, 1.4 eq.) are added dropwise at 20/25° C. over a period of 1 hour. Upon complete addition, the suspension thus obtained is stirred for 2 hours at 20°/25° C. The salts are filtered in an inert nitrogen atmosphere, washing them with 160 ml toluene; the organic solution is then concentrated to a small volume under vacuum and used as such in the subsequent step.

Example 21

N-6,6-trimethyl-N-trimethylsilyl-trans-hept-2-en-4-inamine 113.0 g (0.738 mol) 1,1-dichloro-3,3-dimethylbutene and 565 ml toluene are introduced into a reactor. The resulting solution is heated to 80° C., and then, having reached said temperature, over a period of 1.5 hours, 557 ml of 25% n-butyllithium (2.1 eq.) in heptane are added.

Upon complete addition, the suspension is stirred for 2 hours at 80° C. A mixture consisting of toluene, heptane and chlorobutane, reaction by-product, is then subsequently distilled at atmospheric pressure under a flow of nitrogen, at the same time adding toluene in order to keep the initial volume constant.

The suspension is cooled to 65°/70° C., then the N-trimethylsilyl-trans-1-methylamino-3-chloro-2-propene toluenic solution from example 20, corresponding to 100 g theoretical (0.564 mol, 0.76 eq.) is added followed by 170 ml THF and 730 mg $NiCl_2$ (0.76% mol). The reaction mixture is heated at 80° C. After 2 hours it is cooled to 20°/25° C. and the reaction mixture is then quenched in a second reactor containing 565 ml water and 113 ml of 30% ammonia. 4.3 g acticarbon (5% wt.) is then added and the mixture stirred for 30 minutes and then filtered, washing the carbon with 128 ml toluene, separating the phases and washing the organic phase with 256 ml water and then subsequently extracting the combined aqueous phases with 256 ml toluene. Finally, the combined organic phases are concentrated to a small volume. The product, N-6,6-trimethyl-N-trimethylsilyl-trans-hept-2-en-4-inamine is obtained with a yield of 74.4% (as determined by GC with internal standards).

$^1$H-NMR (DMSO, TMS, ppm): 0.1 (s, 9H, Si(CH$_3$)$_3$); 1.20 (s, 9H, C(CH$_3$)$_3$); 2.23 (s, 3H, N—CH$_3$); 3.09 (dd, 2H, CH$_2$, J=5.87, 1.69 Hz); 5.55 (dt, 1H, CH, J=15.84, 1.70 Hz); 5.87-5.97 (m, 1H, CH).

MS (m/e): 222, 208, 166, 73.

Example 22

Terbinafine (1)

The above crude N-6,6-trimethyl-N-trimethylsilyl-trans-hept-2-en-4-inamine toluenic solution (0.420 mol, example 21) is introduced into a reactor along with 59.0 ml of 30% soda (0.588 mol, 1.4 eq.) and 2.6 g of tetrabutylamonium bromide (4% w/w). The mixture is heated to 50° C. and 89 g 1-chloromethylnaphthalene (0.504 mol, 1.2 eq.), diluted in 20 ml toluene, added dropwise over a period of 30 minutes. Upon complete addition, the mixture is heated at 90° C. and after 5 hours it is cooled to 20/25° C. and 245 ml water is added. The phases are separated and extracted with 184 ml toluene and the combined organic phases are washed with 184 ml water. 3.1 g (2.5% w/w) carbon are added to the organic phase, and the suspension stirred at 20° C. for 30 minutes, then filtered and washed with 2×61 ml toluene. Finally, the toluene phase is concentrated to a residue to give 169.9 g (greater than theoretical yield) crude terbinafine. Purity (HPLC A %): 80.6%.

Example 23

Terbinafine (1) hydrochloride 169.9 g (0.420 mol theoretical) crude terbinafine (example 22) is dissolved in 306 ml methyl ethyl ketone (MEK) at 20/25° C.; then 41.3 ml (1 eq.) of 32% aqueous HCl are added dropwise at 20/30° C. Crystallisation of the product takes place during addition. The suspension is stirred for 15 minutes and then concentrated to a small volume under vacuum at 40° C. to azeotropically eliminate the water present, it is subsequently made up twice with MEK and again concentrated to a small volume under vacuum at 40° C. and finally diluted with MEK to restore it to the initial volume. The suspension is then cooled to −10° C. and stirred for 3 hours. The precipitate is filtered, washed with 2×69 ml cold MEK and dried to constant weight under vacuum at 40° C. 103.3 g (0.317 mol, 75% yield) terbinafine hydrochloride are obtained as a white crystalline solid with purity of 99.8% (HPLC A %) and a melting point of 207° C.-208° C.

The invention claimed is:

1. A process for the production of a compound of formula (8):

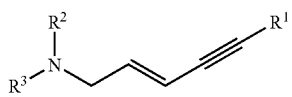
(8)

comprising the step of reacting a compound of formula (6):

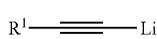
(6)

with a compound of formula (7):

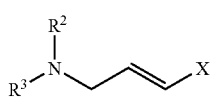
(7)

in the presence of a metal catalyst,
wherein $R^1$ is linear or branched ($C_{1-10}$) alkyl group;
$R^2$ is a linear or branched ($C_{1-10}$) alkyl group;
$R^3$ is an unsubstituted naphthyl ($C_{0-4}$) alkyl group or is a $Si(R^4)_3$ group;
$R^4$ is a linear ($C_{1-5}$) alkyl group;
X is a halogen; and
wherein said metal catalyst is a Ni complex or a Ni salt or mixture thereof.

2. The process according to claim 1 wherein X is selected from chlorine and bromine.

3. The process according to claim 1 wherein the product of general formula (8) is terbinafine or salts thereof.

4. The process according to claim 1 wherein said Ni complex is dichloro bis(triphenylphospine) nickel (II) and said salt is nickel chloride.

5. The process according to claim 1 further comprising the steps:
i) reacting a compound of formula (II):

$R^1—X$ (11)

with a compound of formula (12):

(12)

to give a compound of formula (13):

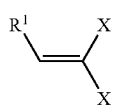
(13)

wherein $R^1$ and X are as defined above, in the presence of a Lewis acid of formula: $MX_n$ (with n=2, 3, 4),
wherein X is a halogen and M is selected from: iron, aluminium, zinc, tin, boron and titanium;
ii) treating the compound of formula (13) with an inorganic base to give a compound of formula (14);

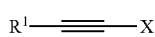
(14)

iii) reacting the compound of formula (14) with an organolithium base of formula $R^5Li$, or with metallic lithium, wherein $R^5$ is methyl, n-butyl, sec-butyl, n-hexyl, cyclohexyl, phenyl, tert-butyl, to give the compound of formula (6).

6. The process according to claim 1, further comprising the steps:
i) reacting a compound of formula (II):

$R^1—X$ (11)

with a compound of formula (12):

(12)

to give a compound of formula (13):

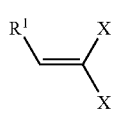
(13)

wherein $R^1$ and X are as defined above, in the presence of a Lewis acid of formula: $MX_n$ (with n=2, 3, 4),
wherein X is a halogen and M is selected from: iron, aluminium, zinc, tin, boron and titanium;

ii) reacting the compound of formula (13) with an organolithium base of formula $R^5Li$, or with metallic lithium, wherein $R^5$ is methyl, n-butyl, sec-butyl, n-hexyl, cyclohexyl, phenyl, tert-butyl, to give the compound of formula (6).

7. The process according to claim 5 wherein, in said step i), X is selected from chlorine and bromine.

8. The process according to claim 5, in said step i), M is selected from iron and aluminium.

9. The process according to claim 1 wherein, in the case of $R^3$ being $Si(R^4)_3$, it includes the step of reacting a compound of formula (17):

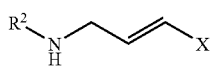  (17)

with a compound of formula (18):

  (18)

in order to obtain a compound of formula (7a):

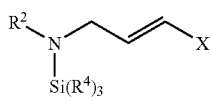  (7a)

wherein $R^2$, $R^4$ and X are as described above.

10. The process according to claim 9 wherein said reaction of the compound of formula (17) with the compound of formula (18) takes place in the presence of an organic base selected from triethylamine, trimethylamine, N-ethyl-diisopropylamine, diazabicyclononane (DBN), and diazabicycloundecene (DBU).

11. The process according to claim 9, further including the step of reacting a compound of formula (15):

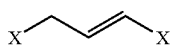  (15)

with a compound of formula (16):

$R^2$—$NH_2$  (16)

to give the compound of formula (17).

12. The process according to claim 11 wherein said reaction of the compound of formula (15) with the compound of formula (16) is carried out through the addition of the compound of formula (15) to an aqueous amine mixture of the compound of formula (16), in molar excess, in the presence of a non-polar organic solvent at a temperature of between 0° and 100° C. for a period of time of 0.5 to 5 hours.

13. The process according to claim 1 wherein, in the case of $R^3$ being $Si(R^4)_3$, it additionally includes the following steps:

iv) deprotecting a compound of formula (8a):

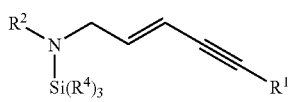  (8a)

by aqueous work-up, optionally in the presence of acids or bases, to give a compound of formula (8b):

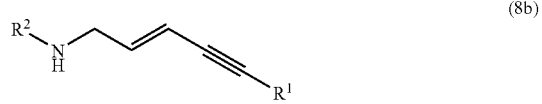  (8b)

v) reacting the compound of formula (8b) with a compound of formula (19):

$R^3$—X  (19)

to give the compound of formula (8).

14. The process according to claim 1 wherein, in the case of $R^3$ being $Si(R^4)_3$, it additionally includes reacting a compound of formula (8a):

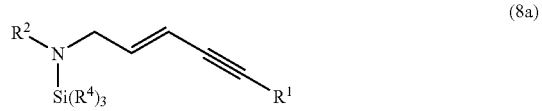  (8a)

with a compound of formula (19):

$R^3$—X  (19)

to give the compound of formula (8).

15. The process according to claim 14 wherein said reaction of the compound of formula (8a) with the compound of formula (19) takes place in the presence of an inorganic base selected from: sodium or potassium hydroxide, sodium or potassium carbonate, sodium or potassium acetate.

16. The process according to claim 14 wherein said reaction of the compound of formula (8a) with the compound of formula (19) takes place in a biphasic aqueous-organic system, optionally in the presence of a phase transfer catalyst selected from: tetrabutylamonium bromide, tetrabutylamonium bisulphate, tetrabutylamonium hydroxide or cetyl-trimethylamonium chloride.

17. The process according to claim 1 wherein, in the case of $R^3$ being other than $Si(R^4)_3$, the compound of formula (7) is obtained through the reaction of a compound of formula (20):

  (20)

with a compound of formula (15):

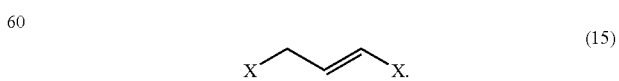  (15)

18. The process according to claim 6 wherein, in said step i), X is selected from chlorine and bromine.

19. The process according to claim 1 wherein X is chlorine.

20. The process according to claim 5, wherein $R^5$ is n-butyl.

21. The process according to claim 5, in said step i), M is iron.

22. The process according to claim 9 wherein said reaction of the compound of formula (17) with the compound of formula (18) takes place in the presence of triethylamine.

23. The process according to claim 12 wherein said non-polar organic solvent is selected from heptane, hexane, pentane, cyclohexane, toluene, xylene, and mesithylene.

24. The process according to claim 12 wherein said non-polar organic solvent is heptane, said temperature is between 15° and 25° C., and said period of time is 1 to 3 hours.

* * * * *